(12) United States Patent
Jangam et al.

(10) Patent No.: US 8,841,127 B2
(45) Date of Patent: Sep. 23, 2014

(54) METHODS AND DEVICES FOR SAMPLE COLLECTION, TREATMENT AND DISPENSING

(75) Inventors: Sujit Rao Jangam, San Mateo, CA (US); Abhishek K. Agarwal, Evanston, IL (US); Robert Elghanian, Wilmette, IL (US); David M. Kelso, Wilmette, IL (US)

(73) Assignee: Northwestern University, Evanston, IL (US)

(*) Notice: Subject to any disclaimer, the term of this patent is extended or adjusted under 35 U.S.C. 154(b) by 539 days.

(21) Appl. No.: 13/026,047

(22) Filed: Feb. 11, 2011

(65) Prior Publication Data

US 2011/0212482 A1 Sep. 1, 2011

Related U.S. Application Data

(60) Provisional application No. 61/304,029, filed on Feb. 12, 2010.

(51) Int. Cl.
*A61B 5/151* (2006.01)
*C12Q 1/02* (2006.01)
*A61B 5/15* (2006.01)
*G01N 1/28* (2006.01)
*B01L 3/00* (2006.01)

(52) U.S. Cl.
USPC ............. 436/17; 436/180; 422/522; 422/514; 422/513; 422/501

(58) Field of Classification Search
USPC .......... 422/500, 501, 513, 514, 520, 521, 522
See application file for complete search history.

(56) References Cited

U.S. PATENT DOCUMENTS

| | | | | |
|---|---|---|---|---|
| 2,237,213 | A * | 4/1941 | Brown | 73/864.02 |
| 4,250,893 | A | 2/1981 | White | |
| 4,411,163 | A | 10/1983 | White | |
| 4,576,185 | A * | 3/1986 | Proud et al. | 600/573 |
| 5,916,813 | A | 6/1999 | Gorog | |
| 7,344,506 | B2 | 3/2008 | Scampini | |
| 2004/0152206 | A1 * | 8/2004 | Davis et al. | 436/514 |
| 2007/0173737 | A1 | 7/2007 | Scampini | |
| 2010/0092979 | A1 | 4/2010 | Kelso et al. | |

FOREIGN PATENT DOCUMENTS

JP 10-221334 A 8/1998
WO 83/00281 A1 2/1983

OTHER PUBLICATIONS

Heimdahl, A. et al. "Detection of anaerobic bacteria in blood cultures by lysis filtration." Eur J Clin Microbiol (1985) 4 404-407.*
International Search Report from related PCT Patent Application No. PCT/US2011/024605 mailed Oct. 27, 2011, Application now published as International Publication No. WO2011/100595 on Aug. 18, 2011.

* cited by examiner

*Primary Examiner* — Christopher A Hixson
(74) *Attorney, Agent, or Firm* — Jacqueline F. Mahoney; Judy M. Mohr; McDermott Will & Emery LLP (57) ABSTRACT

A device for collecting, treating and dispensing a biological sample is described. Use of the device permits integration of sample collection, sample treatment, and sample dispensing.

14 Claims, 7 Drawing Sheets

Fig. 7

METHODS AND DEVICES FOR SAMPLE COLLECTION, TREATMENT AND DISPENSING

CROSS-REFERENCE TO RELATED APPLICATION

This application claims priority to U.S. Provisional Application Ser. No. 61/304,029 filed Feb. 12, 2010, which is herein incorporated by reference in its entirety.

TECHNICAL FIELD

The present subject matter relates to devices for integration of sample collection, treatment, and dispensing, and to methods of using the devices.

BACKGROUND

Collection and analysis of biological samples, especially biological samples from human subjects, is needed for a variety of analytical tests. As molecular level diagnostics continue to become readily available at point of care environments, devices for collecting, processing, and dispensing biological samples are needed. For example, blood and other body fluids are commonly collected and submitted to determine whether a particular analyte is present or absent. Determination of viral infections from a blood sample requires processing of the blood to lyse the blood cells and/or viral particles, to release the DNA or RNA, as the case may be, for amplification and detection. Devices and methods are needed that minimize manipulation, transfer, and processing steps of a biological sample, to improve efficiency and safety in preparing a biological sample for subsequent analysis.

BRIEF SUMMARY

In a first aspect, a device comprising a tubular capillary member and a compressible bulb member defining a bulb-shaped chamber is provided. The tubular member and compressible member are, in one embodiment, separate, discrete physical components detachable from one another, but configured for engagement with one another. In one embodiment, the device further comprises an opening that functions as an air vent. In embodiments wherein the device does not comprise an air vent, the tubular member is preferably detachable from the compressible member, and when in an engaging relationship define a gap between the members that is in fluid communication with the external environment.

In one embodiment, the tubular member is separable from and insertable into the bulb member. The members when inserted into one another each have a region that overlaps with the other. In one embodiment, a reagent is present in the chamber defined by the bulb member, and in an exemplary embodiment the reagent is a lysing reagent or an anti-coagulation reagent. When at least a lysing reagent is present in the bulb-shaped chamber, the chamber is referred to herein as a lysing chamber. The bulb member, and the lysing chamber defined by the bulb member, can have various shapes including a compressible or flexible bulb at one end and an elongated member or neck at the other end, the neck sized to receive the tubular member.

In another aspect, provided is a device wherein a capillary collection tube is detachably connected to a flexible bulb member that defines a chamber, and wherein blood is collected in the capillary collection tube by compressing and releasing the flexible bulb member, and wherein blood is dispensed from the device by detaching the collection tube and compressing or squeezing the bulb member to dispense blood, preferably treated blood, from the bulb chamber.

In one embodiment, the bulb member comprises a first end for receiving the capillary tube, the first end having an inner diameter greater than an outer diameter of the capillary tube. In another embodiment, the inner diameter of a neck region of the bulb member and the outer diameter of the capillary tube differ by an amount to define a gap when the capillary member is inserted into the neck region of the bulb member. In various embodiments, the gap is at least about 0.1 mm, 0.2 mm, or 0.25 mm, or alternatively is between about 0.1-0.25 mm, preferably between about 0.2-0.25 mm.

In still another embodiment, the device further comprises an opening, to function as an air vent, the opening positioned on the flexible material of which the bulb member is made. In an alternative embodiment, the device further comprises an opening that functions as an air vent, the opening preferably disposed an interface between the outer surface of the capillary collection tube and the outer surface of the bulb member, and preferably of an outer surface of a neck region of the bulb member. In some embodiments, an inner surface of at least a portion of the bulb member having a region through which a collection tube can be inserted comprises one or more ribs, thereby forming gaps that serve as air vents when the bulb member and the collection tube are removingly inserted.

In another embodiment, an opening is disposed on the bulb member, and a venting tube is inserted into, connected to or integral with the opening on the bulb member.

In yet another embodiment, the opening or air vent is closed or plugged with a gas permeable, liquid impermeable membrane.

In some embodiments the capillary collection tube and squeezable, flexible bulb member are constructed from different materials. In one embodiment, the capillary collection tube is constructed from glass and the squeezable bulb member that defines a lysing chamber is constructed from a flexible plastic, and in one embodiment from a thermoplastic material.

In one embodiment, the capillary collection tube and the squeezable bulb member comprise a single, integral and inseparable unit. An opening in at least the bulb member is provided to permit movement of fluid and air in, through and out of the device.

In another embodiment, a device for collecting, lysing, and dispensing blood is provided. The device comprises a receiving tube defining a tube volume and a flexible bulb-shaped component defining a chamber volume, wherein the tube volume is less than half of the chamber volume. In some embodiments the receiving tube comprises a beveled or tapered end or edge.

In another aspect, methods for collecting and dispensing a biological sample using a device as described herein are provided. In a preferred embodiment of the method, a lysing agent is included in the device, and the method additionally provides for lysing a component in the sample, such as a cell, bacterium or virus, to release intracellular components. In a preferred embodiment, the biological sample is blood, and a blood sample is collected and treated with a lysing agent to lyse all the cellular components of blood including red blood cells (RBC) and white blood cells (WBC). Genomic DNA from the blood cells is released in the lysate which can then be dispensed from the device for further processing.

In addition to the exemplary aspects and embodiments described above, further aspects and embodiments will become apparent by reference to the drawings and by study of the following descriptions.

DETAILED DESCRIPTION

The present disclosure relates to a device designed to perform the integrated functions of sample collection, treatment and dispensing. The sample can be any biological sample, such as but not limited to saliva, urine, lymph, mucus, sputum, or blood, and in a preferred embodiment, the sample is blood. As will be described below with reference to the drawings, the device is particularly suited for collection of a blood sample and for treating the sample to release genomic DNA/RNA from constituents in the sample. After treating the sample, it can be dispensed from the device and then the device is discarded Accordingly, in a preferred embodiment, the device is a disposable, single use unit. As will also be described below, some embodiments of the device provide for precise control over the volume of sample collected, treated and dispensed.

Figure 1:
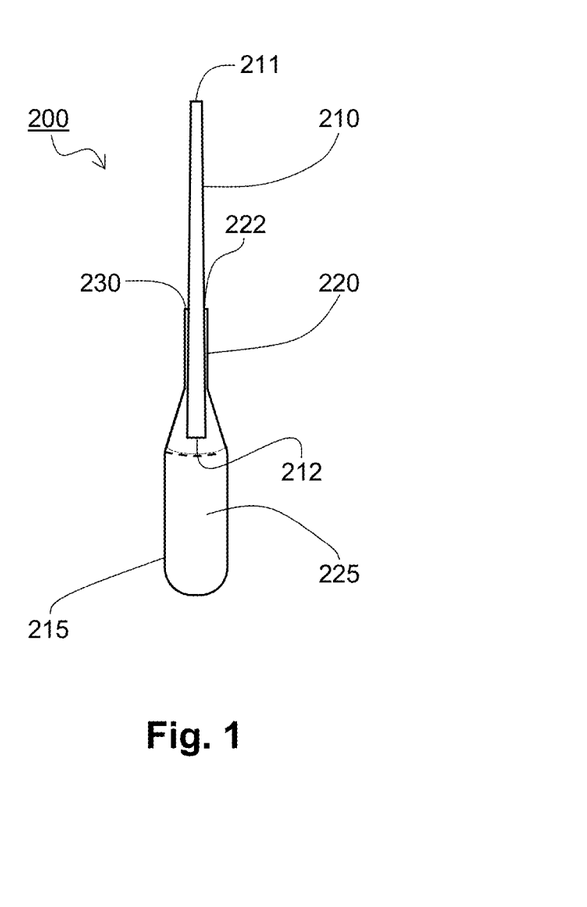
FIG. 1 shows a device, according to one embodiment, for blood collection, lysing, and dispensing.

A first embodiment of the device is illustrated in FIG. 1. Device 200 comprises a capillary tube 210 and a compressible bulb-shaped member 215 that defines an open chamber 225. Capillary tube 210 has a first open end 211 and a second open end 212. An open channel within the tube connects the first and second open ends. Compressible member 215 tapers at one end to form a neck region 220 with an opening 222. As can be appreciated from the drawing, the outer diameter (OD) of the capillary tube, or of at least one of the two ends of the capillary tube, is slightly smaller than the inner diameter (ID) of the opening in the neck region of the compressible member, so that an end of the capillary tube can be inserted into the opening in the neck region as illustrated. The difference in the OD of the capillary tube and the ID of the tapered neck region defines a gap 230. The gap functions as an outlet or vent for air that is displaced as the compressible member is squeezed or compressed to create a negative, sub-atmospheric pressure within the chamber. Accordingly, in this embodiment, the air vent in the device is at a junction between an end of the capillary tube and the compressible member, and more specifically at a junction between an end of the capillary tube and an opening in the compressible member.

In use, the compressible member is squeezed to remove the air in the chamber, the air exiting the chamber via the air vent. Release of the compressible member then allows a sample fluid, such as blood, in contact with the opening at the distal end of the capillary tube to flow into the capillary tube, thereby collecting a sample into the device. In some embodiments, the capillary tube fits very tightly into the opening in the neck of the bulb, and the compressible bulb member is squeezed prior to sample collection as simple fluid flow by capillary action into the capillary tube will not otherwise occur. In some embodiments, the OD of the capillary tube is about 2 mm while the ID of the opening in the neck of the compressible member is about 2.5 mm, defining an annular gap of 0.25 mm. More generally, the annular gap between the outer surface of the capillary tube and the inner surface of the opening in the neck of the compressible member is between about 0.1 mm to about 0.5 mm.

The chamber defined by the bulb-shaped compressible member can include a reagent, such as a lysing reagent and/or an anti-coagulant. In embodiments where the chamber comprises a lysing reagent that has activity to lyse cells, viral or bacterial particles, the chamber is referred to as a lysing chamber.

The capillary tube can be used for measuring the blood that enters the chamber. The length and diameter of the capillary tube designate the maximum amount of blood that can enter the chamber. In some embodiments, the device is used to obtain between 10-200 µL of a sample, preferably blood. In some embodiments, a mark or a series of graduations are affixed on the capillary tube to designate specific volumes.

Figure 2A:
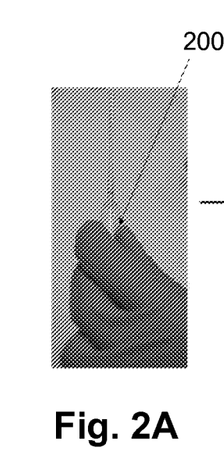
FIGS. 2A-2D illustrate an exemplary protocol for using a device according to FIG. 1, for the collection, treatment and dispensing of a biological sample, such as blood.
Figure 2B:
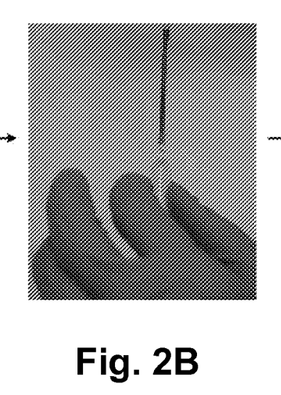
Figure 2C:
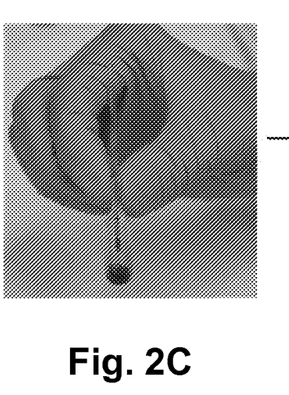
Figure 2D:
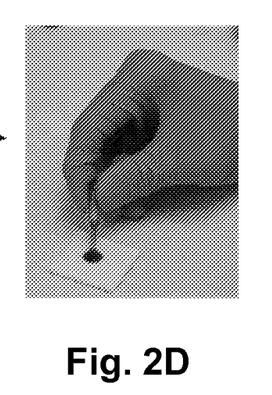

Use of device 200 for collection, treatment and dispensing a blood sample is illustrated in FIGS. 2A-2D. A user holds the device, generally with the compressible bulb-shaped member between the thumb and forefinger (FIG. 2A). The bulb-shaped member is compressed, to displace air in the chamber. After puncture of the collection site on a patient, the distal tip of the capillary tube of the device is contacted with the blood drop formed at the collection site. Compression on the bulb-shaped member is released, to permit blood flow into the capillary tube by capillary action, and as in FIG. 2B, preferably to pre-printed mark on the capillary tube. The blood sample flows into the lysis chamber, and the user can gently agitate the device to effect mixing of the sample with the reagent in the chamber, as illustrated in FIG. 2C. Agitation can be done by swirling the chamber contents, by tapping the bulb member with a finger or by tapping the bulb member on a surface, which places the capillary tube in a vertical orientation ensuring the sample volume remains in the chamber. Interaction of the blood with the reagent present in the chamber is effected. In a preferred embodiment, the lysis reagent is pre-coated on the walls of the lysing chamber, and an exemplary coating procedure is provided in Example 1. Prior to dispensing the treated sample from the device, the capillary tube is removed from its collection position wherein an end of the capillary tube is inserted into the opening in the neck region of the compressible bulb-shaped member. The treated (lysed) blood is then dispensed from the device into or onto another surface, chamber or vessel for further processing or analysis. FIG. 2D shows the blood sample being dispensed onto a filter separator by inverting the bulb-shaped member and squeezing the bulb to dispense it therefrom.

A skilled artisan will appreciate that the volume of the chamber can be varied depending on the amount of sample to be collected. The volume of air in the inverted chamber should be greater than or equal to the volume of the sample being collected so as to completely expel the sample during dispensing. The positive pressure (i.e., squeezing the bulb) required to dispense the blood minimizes any spillage.

Figure 3:
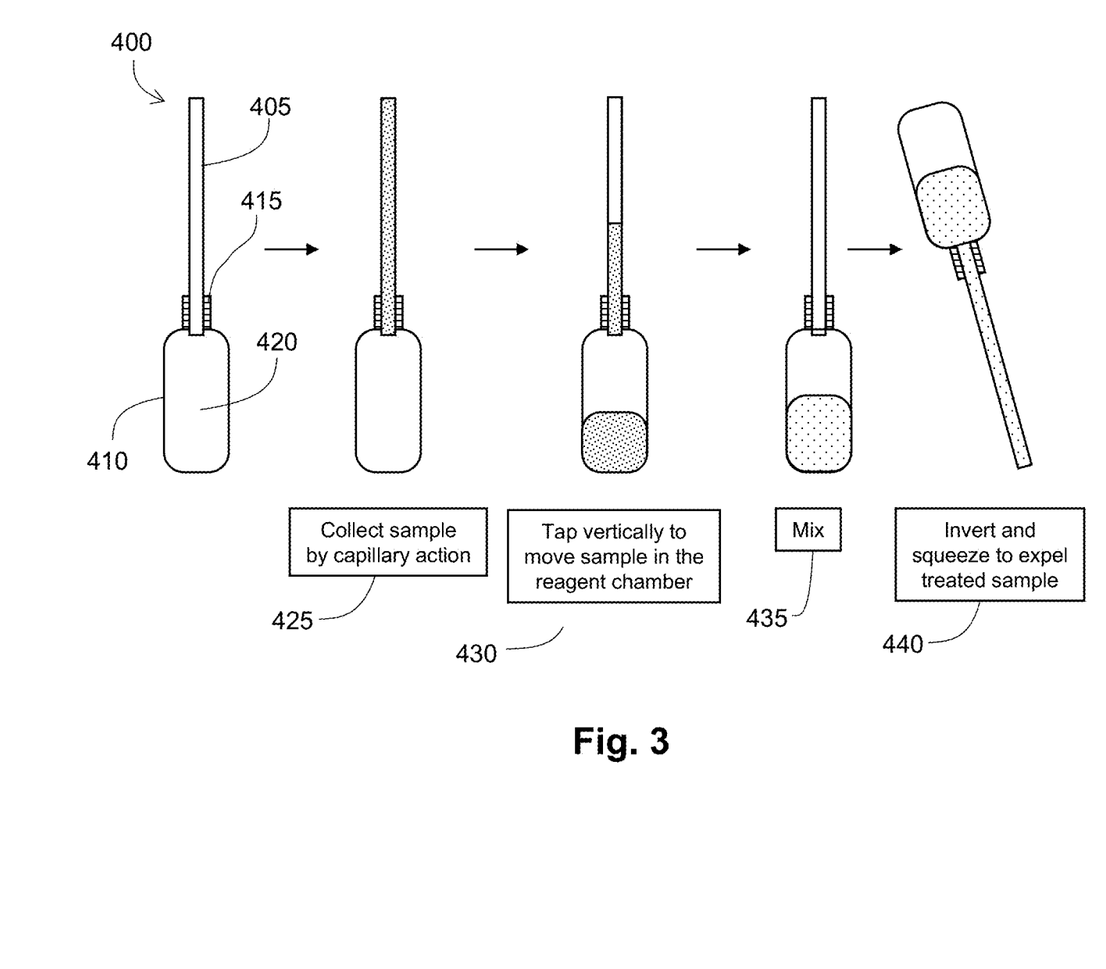
FIG. 3 shows another exemplary device according to another embodiment, to collect, treat, and dispense blood.

Another embodiment of a device is illustrated in FIG. 3. A device 400 comprises a capillary tube 405 and a bulb-shaped member 410, with a liquid-tight, gas permeable membrane 415 situated between the juncture of the tube and member 410. In use, the gas permeable membrane allows a sample, such as blood, to flow into the capillary tube 410 by capillary action, as air is vented through the gas permeable membrane, as indicated at 425 in FIG. 3. The device is agitated, preferably with the collection tube in a vertical position as indicated at 430, to collect the sample in the chamber defined by the bulb-shaped member, which in this embodiment is pre-coated with a lysis reagent and is accordingly referred to as a lysis chamber 420. The lysis chamber and sample are mixed, as indicated at 435, by swirling or finger tapping, to mix the lysing reagent with the sample, creating a treated sample. The device is then inverted, as shown in 440, and the lysing chamber is compressed or squeezed to expel the treated sample from the lysis chamber. The presence of the liquid-tight and gas-permeable membrane makes removal of the capillary tube unnecessary.

A skilled artisan will appreciate that the capillary tube in the device of the various embodiments described herein can be made of virtually any materials, with glass or a plastic material preferred. The compressible member can be made of a variety of flexible, compressible materials, including plastics and thermoplastics. In one embodiment, the capillary collection tube is made of a material that is different from the material forming the compressible member.

Figure 4A:
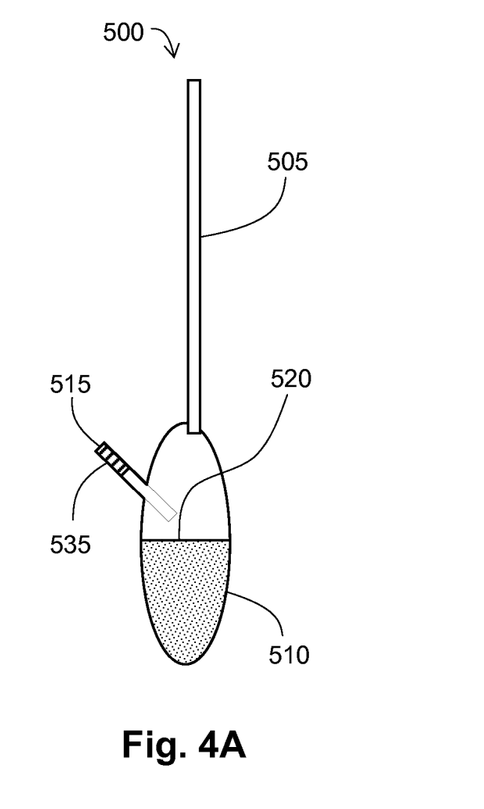
FIGS. 4A-4B show another device in accord with another embodiment that permits precise collection, lysing, and dispensing of a biological sample.
Figure 4B:
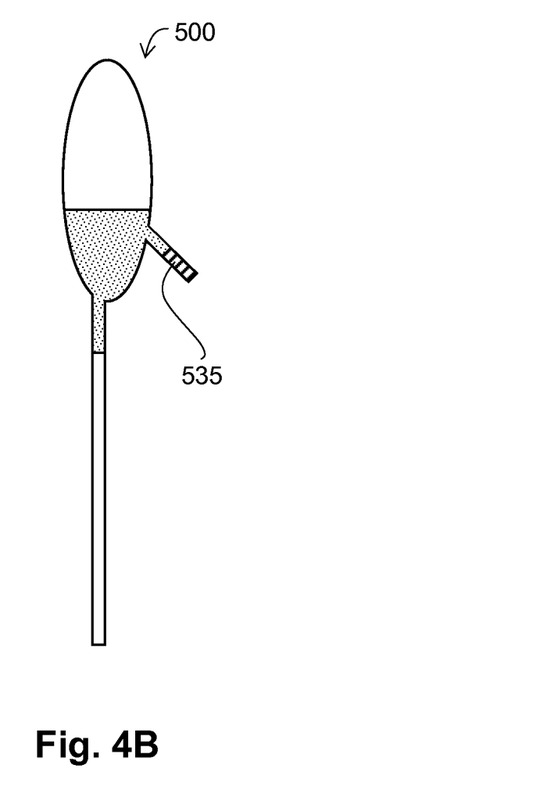
Figure 5:
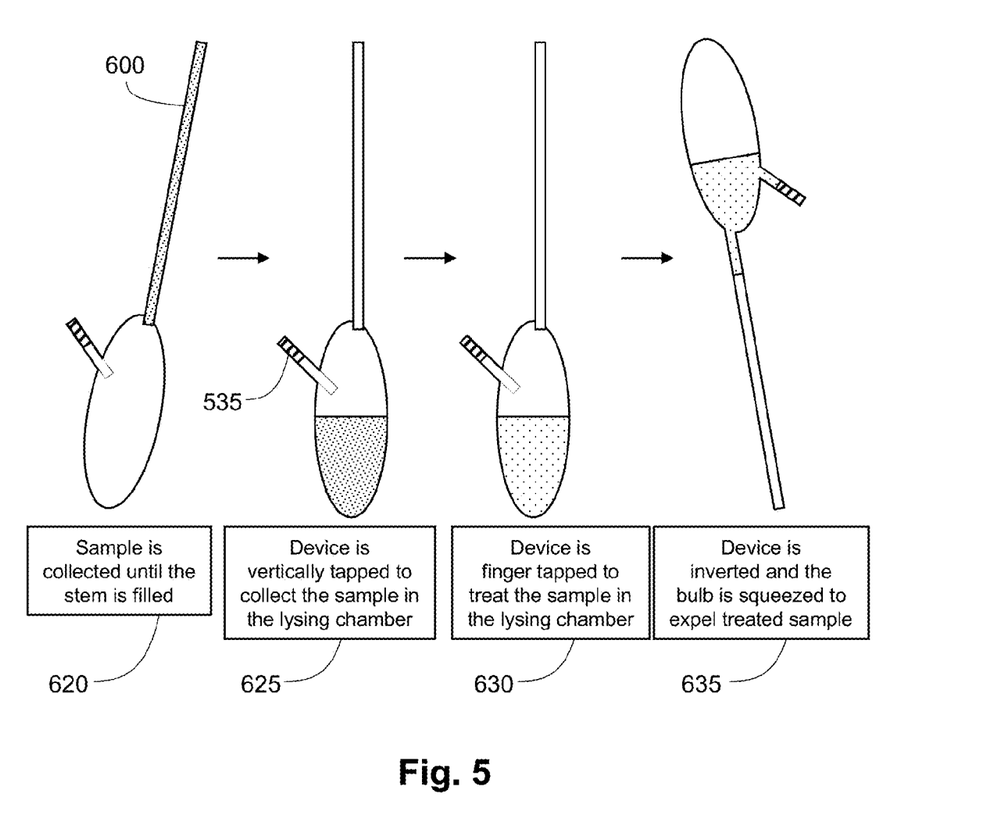
FIG. 5 shows an exemplary protocol for sample collection, treatment, and dispensing of an embodiment of a device described herein.

Another embodiment of a device is illustrated in FIGS. 4A-4B. A device 500 comprises a stem or receiving tube 505 for metered sample collection and a squeezable bulb member 510, which defines a chamber referred to as a lysing chamber when a lysing reagent is present in the chamber, and comprises an air-vent 515. The length and diameter of the stem can be used to measure the amount of sample 520 collected. The lysing chamber is pre-coated with reagents, such as one or more of a lysing agent and an anticoagulant. The air vent 515 is sealed or occluded with a gas permeable, liquid impermeable membrane 535 that prevents liquid sample from leaking out the air vent but permits air to enter and exit the lysing chamber. A variety of materials are suitable for membrane 535, with a hydrophobic polypropylene membrane exemplary. In use, and now with reference to FIG. 5, the stem is contacted with the source of fluid sample 600 which flows into the stem by capillary action. The dimensions of the stem control the volume of sample taken from a collection site, and in this example the stem is filled with sample, as shown at 620 in FIG. 5. The hydrophobic gas-permeable, liquid impermeable membrane 535 permits release of air from the chamber and stem, as the fluid sample enters the device. The device is then agitated, such as by tapping on a surface, with the stem in a vertical orientation as shown in step 625, to facilitate the sample entrance into the bulb from the stem. The air vent is positioned such that the sample level in the bulb is lower, preventing the sample from prematurely blocking the air vent. During agitation, the fluid sample is treated with the reagents in the chamber, as indicated at step 630, thereby forming a treated sample. After treatment, the treated sample is dispensed from the device as illustrated in 635, by inverting the device and compressing the bulb. As the device is inverted, the location of the air vent below the level of sample ensures that the air vent is blocked by treated sample. On application of positive pressure (e.g., in the form of bulb squeezing), the treated sample can only flow out of the stem. If needed, the air vent may be blocked with a finger to ensure complete dispensing of treated sample. The volume of the chamber can be varied depending on the amount of sample. The volume of air in the inverted chamber should be greater than the volume of sample being collected so as to completely expel the sample during dispensing. The positive pressure (e.g. squeezing the bulb) required to dispense the sample minimizes any spillage.

Figure 6A:
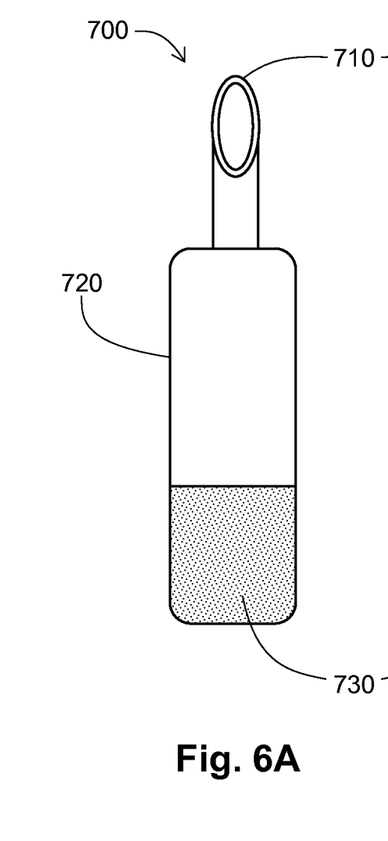
FIGS. 6A-6B show an exemplary device according to yet another embodiment, the device providing precise collection, treating, and dispensing of a biological fluid.
Figure 6B:
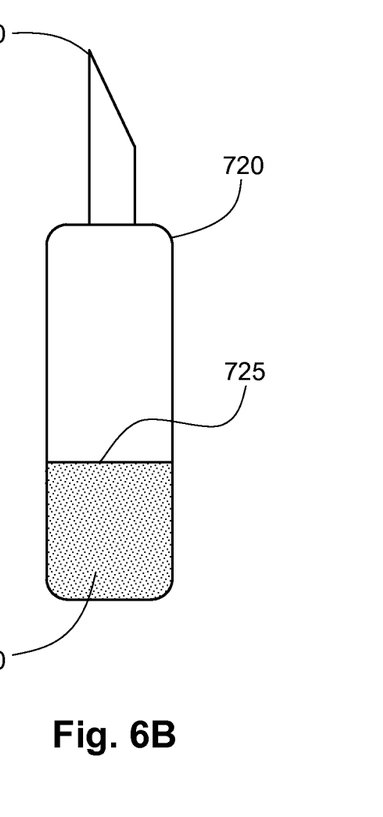
Figure 7:
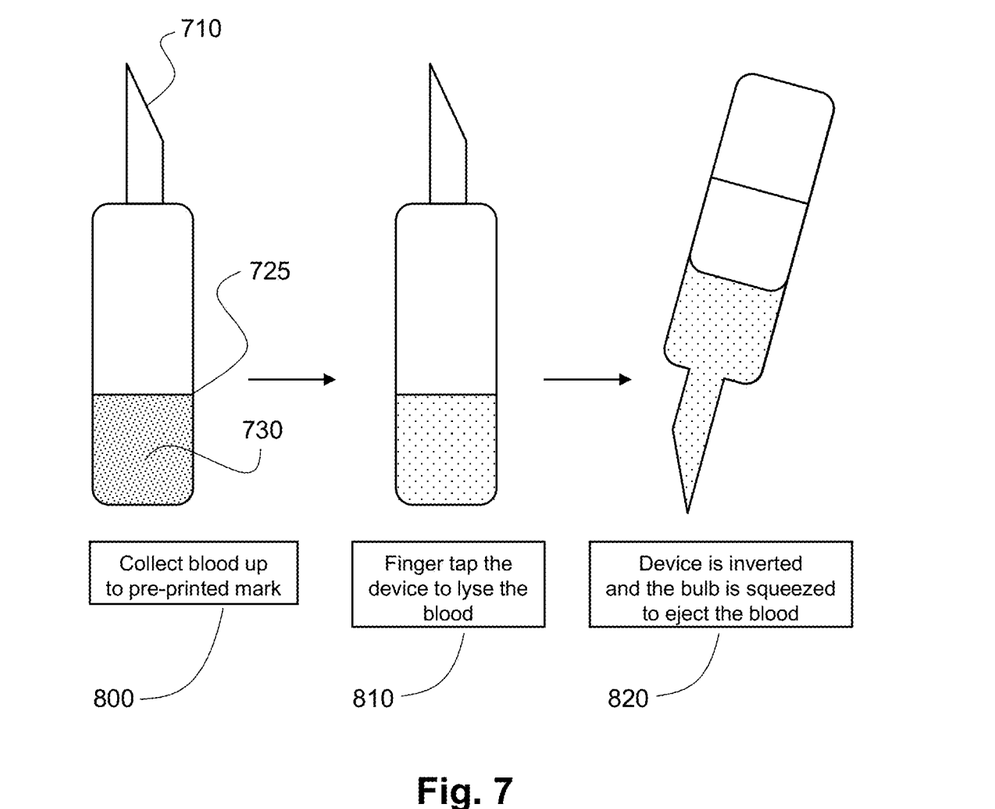
FIG. 7 shows an exemplary protocol using a device according to FIGS. 6A-6B for sample collection, treatment, and dispensing.

Yet another embodiment is illustrated in FIGS. 6A-6B. A device 700 comprises a single part, unitary device having a squeezable bulb 720, which also serves as a lysing chamber when a lysing reagent is present in the chamber, and a receiving tube 710 that defines a tube volume, the receiving tube for collection of sample (e.g., blood) from a collection site. In this embodiment, the receiving tube has a beveled distal end that maximizes surface area for contact with a sample at a collection site. During sample collection, the bulb is compressed slightly and the distal tip of the receiving tube is contacted with the sample at the collection site, such as a skin puncture site for collection of a blood sample. The pressure applied on the bulb during squeezing is released slowly to allow blood 730 to flow into the chamber up to the level mark 725 on the receiving tube. With reference now to FIG. 7, after collection of a sample, such as a blood sample (step 800), the device is gently agitated, such as by tapping with a finger or swirling gently, to mix the blood for lysis, as shown in step 810. To dispense the lysed blood, the device is inverted and the bulb is squeezed in step 820.

In all of the embodiments of the devices described herein, the volume of the chamber can be varied depending on the amount of sample required. The volume of air in the chamber typically is greater than or equal to the volume of the sample being collected so as to completely expel the sample during dispensing. The positive pressure (e.g., squeezing the bulb) used to dispense the sample minimizes any spillage. To allow for a sufficient quantity of air in the chamber, the volume of sample capable of being held in the receiving tube is less than half of the volume of chamber so that during collection of the sample greater control is afforded to the operator in controlling the number squeezes and/or in regulating the pressure of the squeeze necessary to fill the chamber with the desired amount of sample. In a preferred embodiment, the volume in the receiving tube is less than half of the chamber volume.

Merely for illustration, the compressible member is shown as a bulb-shaped member. It will be appreciated that other shapes are equally functional, such a tear-shaped or elongated rectangular.

As mentioned above, the chamber in the devices described herein can comprise a lysing reagent in the compressible bulb-shaped member. The reagent can be coated onto the was of the bulb-shaped member, or can be a particulate material disposed in the chamber. Exemplary lysing reagents include detergents and surfactants, such as a non-ionic surfactant, such as those with a hydrophilic polyethylene oxide head group and a hydrocarbon group such as tetramethylbutyl-pheynl (e.g. Triton™), a polyoxyethylene surfactant (Brij®), polysorbate detergents (Tween®), ethylene oxide-propylene oxide triblock copolymer (Pluronic®) or sodium dodecyl sulfate (SDS). Exemplary and preferred lysing agents are Triton™-X-100, nonyl phenoxypolyethoxylethanol (NP-40) and Tween®-20. The chamber can also include, alone or in combination with a lysing reagent, an anti-coagulant, particularly for when the sample being collected and treated is blood. Exemplary anti-coagulants include heparin and warfarin. The reagent(s) can be deposited in the chamber using spray drying, lyophilization, or solvent coating methods. In some embodiments the lysing reagent coats only a portion of the lysing chamber.

In one embodiment, a precise amount of a low melting point (liquid) detergent, such as Triton-X-100, NP-40 or Tween-20, is deposited in the device and is used to lyse cells in blood when it is collected in the collection device. The delivery of a precise amount of detergent ensures efficient cell lysis and minimizes any inhibition of subsequent molecular assays such as amplification of nucleic acids by PCR, due to excessive detergent. Example 1 provides a procedure for coating the inner walls of the chamber with a selected amount of a reagent. A skilled artisan will appreciate that other methods of coating or dispensing a fixed amount of reagent include spray drying and lyophilization. In one embodiment, provided is a simple and inexpensive method using organic solvents to deliver precise amounts of a detergent applied to the chamber in the compressible bulb of the devices described herein. This method of coating/delivery can be scaled up for manufacture of blood collection devices with lysing agents that are soluble in organic solvents, such as methanol and acetone. A solution of the detergent, such as Triton-X-100, in a low boiling point organic solvent is added to a device as described herein. The device is then heated such as in an oven to evaporate the organic solvent resulting in a device wherein a portion of the lysing chamber is coated with a precise amount of detergent.

The devices and methods of the present disclosure in incorporating a squeezable lysing chamber also provide advantages over collection devices not having this feature in that dispensing blood requires active engagement of the lysing chamber (bulb can be squeezed with variable positive pressure by an operator), thereby affording the operator more control over blood dispensing and preventing accidental spillage of infectious blood.

Blood collection devices are used routinely in clinics for collecting blood specimens for testing for various analytes such as proteins, nucleic acids, sugars, salts and other biomarkers. Devices of the present disclosure are convenient to use because: (a) they do not require manual pipetting and (b) they require active blood dispensing and hence give the operator more control over blood dispensing. Devices of the present disclosure are applied to a variety of applications including PCR and testing for lactate, protein biomarkers and other biological molecules that are released upon cell lysis.

EXAMPLES

The following example is illustrative in nature and are in no way intended to be limiting.

Example 1

Manufacture of Exemplary Device

A device as illustrated in FIG. 1 was prepared by cutting a disposable transfer pipette (Samoa 273, SamcoScientific, San Fernando, Calif.) approximately 4 mm from the end of the stem. A 10 mL solution containing 4% Triton™-X-100 (400 µL) was made in acetone. 100 µL of the Triton-X-100 solution was aliquoted into the cut transfer pipette, which was then placed in a conventional laboratory drying oven at 60° C. for 1-2 hours. The acetone evaporated leaving behind in the bulb member of the pipette 4 µL of Triton-X-100. Then, a capillary tube with an outer diameter of 2 mm (Analox Instruments USA, Lunenburg, Mass.) with a 100 µL capacity was inserted into the cut transfer pipette to form a device as depicted in FIG. 1.

The illustrations of embodiments described herein are intended to provide a general understanding of the structure of various embodiments, and they are not intended to serve as a complete description of all the elements and features of devices and systems that might make use of the structures described herein. Figures are also merely representational and may not be drawn to scale. Certain proportions thereof may be exaggerated, while others may be minimized. Accordingly, the specification and drawings are to be regarded in an illustrative rather than a restrictive sense.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

We claim:

1. A device, comprising:
a capillary collection tube having first and second open ends;
a compressible member that defines a chamber containing a lysing reagent, at least a portion of the first open end of the capillary collection tube being removably inserted at least partially within the compressible member; and
an air vent formed by an annular gap between the compressible member and the capillary collection tube.

2. The device of claim 1, wherein the first end of the capillary collection tube is detachably connected to a neck region of the compressible member, the first end having an outer diameter less than an inner diameter of the neck region.

3. The device of claim 2, wherein the annular gap is between about 0.1 mm to about 0.5 mm.

4. The device of claim 1, wherein the air vent is disposed at a junction where the first end of the capillary connection tube engages the compressible member.

5. The device of claim 1, further comprising a second air vent comprising a stem connected to or integral with the compressible member.

6. The device of claim 1, wherein the air vent is occluded with a gas permeable, liquid impermeable membrane.

7. The device of claim 1, wherein the capillary collection tube and compressible member are constructed from different materials.

8. The device of claim 7, wherein the capillary collection tube is constructed from glass and the compressible member is constructed from plastic.

9. The device of claim 1, wherein the lysing reagent coats a portion of the chamber.

10. The device of claim 1, wherein the lysing reagent is a detergent.

11. The device of claim 1, wherein a volume of the capillary collection tube is less than half of a volume of the compressible member chamber.

12. The device of claim 1, wherein the tube comprises a beveled end.

13. A method for collecting, lysing, and dispensing a sample, comprising:
contacting a fluid sample with a device of claim 1;
agitating the device to mix the sample and the reagent; and
compressing the member to dispense the sample from the device.

14. The method of claim 13, wherein compressing includes or is preceded by detaching the collection tube from the member.

* * * * *